United States Patent [19]

Lahtinen et al.

[11] Patent Number: 5,198,559
[45] Date of Patent: Mar. 30, 1993

[54] N-ACYL AND O-ACYL DERIVATIVES OF N,N-BIS(2,2-DIMETHYL-3-HYDROXY-PROPYL)AMINE, THEIR PREPARATION AND USE

[75] Inventors: Leila Lahtinen, Kulloo; Salme Koskimies, Helsinki; Simo Tuominen, Kulloo; Eija Valtonen, Porvoo, all of Finland

[73] Assignee: Neste Oy, Finland

[21] Appl. No.: 554,415

[22] Filed: Jul. 19, 1990

[30] Foreign Application Priority Data

Aug. 21, 1989 [FI] Finland .................................. 893914

[51] Int. Cl.$^5$ .............................................. C09F 5/00
[52] U.S. Cl. ...................................... 554/35; 560/252; 560/110; 560/105
[58] Field of Search ...................... 560/252, 110, 105; 260/404; 554/35

[56] References Cited

U.S. PATENT DOCUMENTS 3,226,403 12/1965 Magne et al. ...................... 260/404
5,093,142 3/1992 Klemann et al. .................. 260/404

Primary Examiner—Joseph L. Schofer
Assistant Examiner—Peter Mulcahy
Attorney, Agent, or Firm—Steinberg & Raskin

[57] ABSTRACT

The present invention relates to N acyl and O acyl derivatives of N,N-bis(2,2-dimethyl-3-hydroxypropyl)amine which are produced as follows: ammonium halide, sulphate or aldehyde, and isobutyl aldehyde are subjected to condensation reaction and the obtained product is reduced to the corresponding amino alcohol. The hydrogen atoms linked to the nitrogen atom and the oxygen atom are thereafter substituted by acyl groups. The N-acylation and esterification of hydroxyl groups can be performed simultaneously using a carboxyl acid, carboxyl acid halide, or carboxyl acid anhydride. The N,N-bis(2,2-dimethyl-3-hydroxypropyl)amine derivatives can be used as polymer stabilizers, PCV plasticizers, emulsifiers, corrosion resistance agents, and metal complexing agents.

1 Claim, No Drawings

N-ACYL AND O-ACYL DERIVATIVES OF N,N-BIS(2,2-DIMETHYL-3-HYDROXYPROPYL)AMINE, THEIR PREPARATION AND USE

BACKGROUND OF THE INVENTION

It is known in the art that primary and secondary amines react with formaldehyde and isobutyl aldehyde (EP 46288, and Arch. Pharmaz. 308/75 p. 352), generating either direct-chain or cyclic Mannich reaction products (equations 1 and 2).

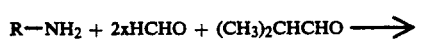

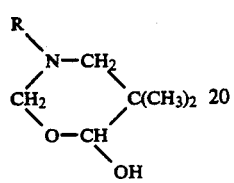

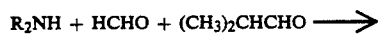

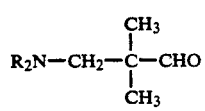

SUMMARY OF THE INVENTION

The present invention relates to new N-acyl and O-acyl derivatives of N,N-bis(2,2-dimethyl-3-hydroxypropyl)-amine, their production procedures and uses.

The formula of the new compounds of the invention is as follows:

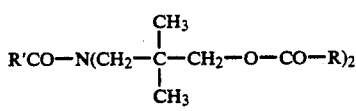

wherein R and R' are the same or different $C_1$–$C_{10}$ alkyl or aryl groups.

It is accordingly, a primary object of the present invention to provide new N-acyl and O-acyl derivatives of N,N-bis(2,2-dimethyl-3-hydroxypropyl)amine.

It is another object of the present invention to provide methods of producing the N-acyl and O-acyl derivatives of N,N-bis(2,2-dimethyl-3-hydroxypropyl)amine.

It is yet a further object of the present invention to provide new plasticizers and stabilizing agents for polymers, lubricating agents, emulsifiers, corrosion resistant agents and metal complexing agents, namely the new N-acyl and 0-acyl derivatives of N,N-bis(2,2-dimethyl-3-hydroxypropyl)amine.

Other objects and advantages of the present invention will be apparent from a further reading of the specification and of the appended claims.

With the above objects in view, the present invention mainly comprising new N-acyl and O-acyl derivatives of N,N-bis(2,2-dimethyl-3-hydroxypropyl)amine of the formula:

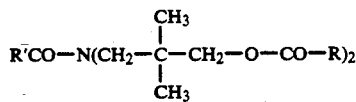

wherein R and R' are the same or different $C_1$–$C_{12}$ (preferably $C_1$–$C_{10}$) alkyl, aralkyl or aryl groups.

In accordance with the present invention, a modified Mannich reaction is used as an intermediate step to product the new N-acyl derivatives of N,N-bis(2,2-dimethyl-3-hydroxypropyl)amine according to the following reaction equations (3–5):

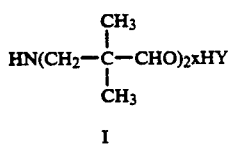

This condensation reaction (3), in which the group Y can be a halide of sulphate, can be performed at 50° to 90° C. in about three hours, either in refluxation conditions or under slight over pressure, using paraformaldehyde, trioxane or an aqueous 40% formaldehyde solution as the formaldehyde source.

The resulting compound is thereafter reduced according to the following reaction equation (4):

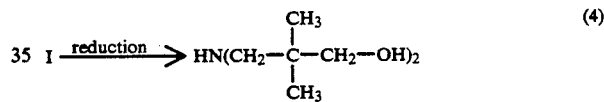

The reduction reaction (4) may be performed using any of several conventional reduction procedures, e.g. by hydrogen reduction in the presence of Ni, Pt, Pd, or of a transition metal catalyst, or by hydride reduction (NaBH4), LiAlH4, etc.). Particularly suitable are e.g. reduction with NaBH4 at 15°–20° C., or with hydrogen in the presence of the Raney-Ni catalyst at 70°–75° C. at 40–55 atm pressure in about four hours.

Thereafter, the reduction product is acylated (equation 5):

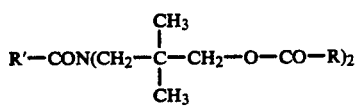

In equation 5, R and R' refer to a same or different alkyl or aryl group which may contain 1 to 12 carbon atoms. X refers to halide or an acyloxy group.

Esterification and N-acylation of the compound II can be performed simultaneously using a suitable carboxyl acid, carboxyl acid chloride or anhydride. For acylation purposes it is also possible to use a mixture of acid chlorides. It is particularly suitable to use the acid chloride at 20°-100° C. with a reaction time of 2 to 20 hrs.

Compounds of formula III above are useful as stabilization agents against oxidation of organic compounds as well as the effect of heat or radiation, and against color formation. Still further, the compounds of the invention are useful for stabilizing polymers, particularly PVC and polyolefines (both homopolymers and copolymers) and as plasticizers for polymers such as PVC. Still further, the compounds are useful as lubricating agents, emulsifiers, corrosion resistance agents and metal complexing agents.

DESCRIPTION OF PREFERRED EMBODIMENTS

The following examples are given to further illustrate the production, identification, testing and use of the compounds of the present invention. The scope of the invention is not, however, meant to be limited to the specific details of the examples.

EXAMPLE 1

Item A

In a reactor provided with a mixer, a reflux condenser and thermometer, 66.9 g ammonium chloride, 162 g formaline and 144 g isobutyl aldehyde, and 1 ml hydrochloric acid were charged. The mixture was heated to 60° C., whereby the isobutyl aldehyde started to reflux. Towards the end of the refluxation the temperature was raised to 80° C. at which temperature the boiling was continued for 2.5 hours.

The obtained condensation product I (362 g), N,N-bis(2,2-dimethyl-3-hydroxypropylaldehyd)amine, was added at 18 to 25° C. to a reactor provided with mechanical stirring, in which 209 g basic (40% NaOH in H20) 12% NaBH4 solution and 500 ml methanol were added. After adding the condensation product, stirring was continued for one more hour, whereafter the water and the methanol were distilled off. The produced boric compounds were dispersed with 1000 ml water by heating in the bain marie. The organic phase was separated when hot, and the product was isolated by vacuum distillation. The product (II), N,N-bis(2,2-dimethyl-3-hydroxypropyl)amine, was identified with IH-NMR spectrophotometer and the GC-MS. The melting point of the product was 28°-30° C., and the yield was 62%.

Item B:

9.5 g of amino alcohol (II) were dissolved in a mixture of dry ether (30 ml) and pyridine (13.0 g). 25.7 g of octanoyl chloride dissolved in ether (10 ml) were added at room temperature, during about five minutes, after which the reaction mixture was refluxed for an additional three hours. The reaction mixture was washed with dilute hydrochloric acid, mild sodium hydroxide solution and, finally, with water to become neutral. The yield of the raw product obtained after the drying and evaporation of the dissolvent was 20 g and the purity of the amino ester was 93%. The product II was identified with the GC-MS system.

EXAMPLE 2

Item A:

The pH of the condensation product (362 g), N,N-bis(2,2-dimethyl-3-hydroxypropyl)amine, obtained as in item A in Example 1 was adjusted to 5 by mild (5%) NaOH solution. The product, 15.0 g of Raney nickel and 100 ml water were added to a 1 liter autoclave provided with a bottom tube. The air was removed from the autoclave by nitrogen-hydrogen rinses. The temperature of the autoclave was raised to 65° C. and the hydrogen pressure to 40 atm. The pressure was maintained almost constant throughout the entire reaction (5 hours) by periodic hydrogen supply.

After being hydrated, the catalyst was centrifuged off and the product was neutralized with 25% NaOH solution. The product released from the salt mode was extracted into diethylether, and the organic phase was dried with sodium sulphate. The raw product obtained after the evaporation of ether was purified by vacuum distillation (125°-150° C., $1-3 \cdot 10^{-3}$ atm). Identification as above. The yield was 54%.

Item B:

9.5 g of the amino alcohol obtained in A (II) were dissolved in a mixture of dry ether (50 ml) and pyridine (13.0 g). 25.7 g of 2-ethyl hexanoyl chloride, dissolved in ether (30 ml) were added at room temperature in about five minutes, whereafter the reaction mixture was refluxed for 7 hours at the boiling point of ether and was thereafter stirred for 20 hours at room temperature. The reaction mixture was washed and treated as in Example I/B. The yield of the raw product II was 19 g and the purity of the amino ester was 94%. The product (III, in which R is 1-ethyl pentyl), N,N-bis(2,2-dimethyl-3-hydroxypropyl)2-ethylhexamide was identified by the GC MS system.

EXAMPLE 3

The reaction described in B of Example 1 was repeated using 9.5 g of amino alcohol II and 25.7 g n-octanoyl chloride, but instead of pyridine, 16.7 g triethyl amine was used. The reaction time was 20 hours. The yield of the raw product, N,N-bis(2,2-dimethyl-3-hydroxypropyl)2-ethylhexamide, was 22 g and purity 72.5%.

EXAMPLE 4

The reaction described in B of Example 1 was repeated with 9.5 g of amino alcohol (II), but instead of the octanoyl chloride, 22.2 g benzoyl chloride were used. The reaction time was 20 hours. The reaction mixture was aftertreated as in Example 1/C. The yield of the yellow oily product, N,N-bis(2,2-dimethyl-3-hydroxypropyl)bentsoacetamide, was 45%. (Identification GC-MS).

EXAMPLE 5

The reaction described in B of Example 1 was repeated, but instead of the octanoyl chloride, 13 g acetyl chloride were used. The yield of the raw product, N,N-bis(2,2-dimethyl-3-hydroxypropyl)acetamide, was 20% and purity 60%.

EXAMPLE 6

15.6 g amino alcohol, 41.9 g pyridine, and 27 g acetic acid anhydride were charged in a 250 ml glass reactor provided with a reflux condenser. The reaction mixture was mixed at 120° C. for about three hours. During the reaction, nitrogen protection gas was used. In the cooled mixture, 40 ml water and 100 ml ether were added. The organic phase was separated and it was washed with mild hydrochloric acid, sodium hydrogen carbonate, and finally, to make it neutral, with water. The yield of the acetamide derivative III was 47%. The product, N,N-bis(2,2-dimethyl-3-hydroxypropyl)acetamide, was identified by the GC-MS; m/e 315 (M+1).

Compounds having the structural formula III, N,N-bis(2,2-dimethyl-3-propionoktanoyl)oktamide, were tested in PVC applications. For instance, a N-octanoyl derivative of dioctanoyl ester of the amino alcohol (R=R'=n heptyl) serves as PVC plasticizer comparable to dioctylphthalate. In addition, the compound A possesses an effect increasing the thermal stability of PVC when used together with Cd/Zn stabilizer. This can be seen in the VDE value representing thermal stability (the thermal stability values are determined according to the VDE standard (3.69)).

| Test | PVC | DOP | A | Stab. | VDE min |
|------|-----|-----|---|-------|---------|
| 1 | 100 | 50 | | | 2.0 |
| 2 | 100 | 50 | | 0.6 | 3.0 |
| 3 | 100 | 45 | 5 | 0.6 | 6.0 |

-continued

| Test | PVC | DOP | A | Stab. | VDE min |
|------|-----|-----|---|-------|---------|
| 4 | 100 | — | 50 | 0.6 | 6.0 |

While the invention has been described with respect to the production of particular compounds and the method of producing the same, it is apparent that variations and modifications of the invention can be made without departing from the spirit or scope thereof.

What is claimed is:

1. N- and O-acyl derivatives of N,N-bis(2,2-dimethyl-3-hydroxypropyl)amine of the formula:

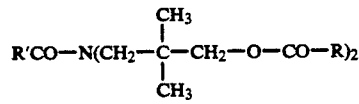

wherein R and R' are the same or different $C_1$–$C_{12}$ alkyl, or $C_6$–$C_{10}$ aryl groups.

* * * * *